(12) United States Patent
    Verrilli

(10) Patent No.: US 11,077,614 B2
(45) Date of Patent: Aug. 3, 2021

(54) LEDGE FORMING SYSTEM FOR PRODUCING A CONJUNCT NOZZLE

(71) Applicant: Brian Leonard Verrilli, Carlsbad, CA (US)

(72) Inventor: Brian Leonard Verrilli, Carlsbad, CA (US)

( * ) Notice: Subject to any disclaimer, the term of this patent is extended or adjusted under 35 U.S.C. 154(b) by 851 days.

(21) Appl. No.: 15/731,955

(22) Filed: Aug. 30, 2017

(65) Prior Publication Data

US 2019/0016047 A1    Jan. 17, 2019

Related U.S. Application Data

(62) Division of application No. 13/694,284, filed on Nov. 15, 2012, now Pat. No. 9,802,031.

(60) Provisional application No. 61/629,187, filed on Nov. 14, 2011.

(51) Int. Cl.
| | |
|---|---|
| *B29L 31/00* | (2006.01) |
| *B29C 65/00* | (2006.01) |
| *B29C 64/209* | (2017.01) |
| *A61M 39/10* | (2006.01) |
| *B29C 65/18* | (2006.01) |
| *B29C 65/56* | (2006.01) |
| *B29C 65/78* | (2006.01) |
| *B33Y 40/00* | (2020.01) |

(Continued)

(52) U.S. Cl.
CPC .......... *B29C 64/209* (2017.08); *A61M 39/10* (2013.01); *B29C 65/18* (2013.01); *B29C 65/568* (2013.01); *B29C 65/7841* (2013.01); *B29C 66/5344* (2013.01); *B29C 66/612* (2013.01); *B29C 66/8161* (2013.01); *B29C 66/81429* (2013.01); *B29C 66/81431* (2013.01); *B29C 66/8322* (2013.01); *A61M 2039/1033* (2013.01); *B29C 64/165* (2017.08); *B29C 64/214* (2017.08); *B29L 2031/7544* (2013.01); *B33Y 40/00* (2014.12)

(58) Field of Classification Search
None
See application file for complete search history.

(56) References Cited

U.S. PATENT DOCUMENTS 3,445,307 A * 5/1969 Balamuth .......... B29C 66/8226
                                            156/73.4
4,409,046 A * 10/1983 Holzwarth .............. A61M 5/32
                                            156/73.6

(Continued)

OTHER PUBLICATIONS

Fisnar, Dispensing Tips, Dispensing Needles, Dispensing Nozzles from Intertronics, Sep. 27, 2011, pp. 10-11. (Year: 2011).*

*Primary Examiner* — Jeffrey M Wollschlager
*Assistant Examiner* — Armand Melendez

(57) ABSTRACT

A novel ledge forming system used to attach a polymer retention hub to a thin wall nozzle core to provide an efficient way to produce a conjunct nozzle. The inventive apparatus provides a means for assembly of components by a method involving use of a press with a heating element to elevate temperature of a thermoplastic polymer to permit formation of a ledge that overhangs the flange of a nozzle core, mechanically locking components together. Execution of the process is rapid, low cost and eliminates damage to the thin wall of the core that would occur if the polymer retention hub were molded around the nozzle core.

20 Claims, 10 Drawing Sheets

(51) Int. Cl.
 *B29C 64/214* (2017.01)
 *B29C 64/165* (2017.01)

(56) References Cited

U.S. PATENT DOCUMENTS

| | | | | |
|---|---|---|---|---|
| 4,802,947 A | * | 2/1989 | Bartholomew ... | A61M 25/0014 |
| | | | | 156/380.5 |
| 4,877,478 A | * | 10/1989 | Cappi ................. | B29C 65/02 |
| | | | | 156/555 |
| 2006/0082156 A1 | * | 4/2006 | Runyan ............... | F16L 33/025 |
| | | | | 285/420 |

* cited by examiner

LEDGE FORMING SYSTEM FOR PRODUCING A CONJUNCT NOZZLE

CROSS REFERENCE TO RELATED PATENTS AND APPLICATIONS

Creation of a Polymer Retention Hub to Form a Conjunct Nozzle Ser. No. 13/694,284
Simplistic Approach to Design of a Reusable Nozzle Hub U.S. Pat. No. 7,434,753 B2
Method of Making a Thin Wall Nozzle U.S. Pat. No. 7,231,716 B2
Deep Drawn Nozzle for Precision Liquid Dispensing U.S. Pat. No. 8,210,455 B2
This application is also entitled to the benefit of Provisional Patent Application Ser. No. 61/629,187 filed Nov. 14, 2011

FEDERALLY FUNDED RESEARCH

Not Applicable

SEQUENCE LISTING OR PROGRAM

Not Applicable

BACKGROUND OF INVENTION

Field of the Invention

This invention pertains to the field of liquid dispensing equipment. More particularly, it pertains to design and method of connection of a molded polymer nozzle hub to a deep drawn nozzle core to construct a conjunct nozzle. The conjoined nozzle forms a unitized assembly through a method of connection that accomplishes this task without the use of adhesives or expensive insert mold tooling that can damage the thin walls of the nozzle core. The nozzle hub is the retention device that holds the core to a luer taper or other outlet and prevents separation under pressure.

Description of the Prior Art

At present, there are five general types of nozzles used for attachment to pumps to extricate a viscous liquid to a work piece: (1) a modified hypodermic or cannula needle made of a polymer hub with stainless steel medical tubing inserted and glued to prevent separation or a metal hub or polymer hub with a band swaged to the medical tube, (2) a custom machined metal needle, (3) a molded plastic cone shaped needle, (4) a ceramic cone shaped needle, (5) a deep drawn nozzle core assembled to polymer hub to form a conjunct or unitized nozzle assembly.

The modified hypodermic or cannula needle is a standard hypodermic needle adapted to fit to a standard luer connection on the outlet of a pump. A medical gage tube is manufactured, cut to size and de-burred. It is inserted into a plastic hub using force and heat. The connection between the two parts is glued with an adhesive to provide a fluid tight seal. Variations of this design style use metal or polymer hubs and swage the hub to the medical tube. Metal hubs are swaged directly; polymer versions use a metal band to provide the compressive force. All of these types are prone to variation in run-out, have restrictive fluid paths and large pressure drops across the exit aperture.

The custom machined metal needle is made of a single piece of material and is shaped to emulate a cannula or is conical in shape. This process is expensive, slow and limits design options. Design of needles using this process are limited to tools that can be made small enough to fit inside the cavity to remove material by cutting. Surface finish is of paramount importance and tool marks and machining ridges only serve to increase the boundary layer and impede flow through restriction as filled fluids agglomerate behind the exit aperture. Machining also limits wall thickness to sections able to withstand the shear force that results from taking a cut. Use of exterior chamfers at the tip thin the wall but dilutes the effect of gravity and increases the propensity for wicking of fluid up the exterior wall.

Molded needles are made of polymer materials and are limited to molding process restrictions. Needles of this type have thick walls and have a difficult time holding tight run out tolerances. The parts are low cost but not suitable for placement of small precision quantities of fluid. Thick walls inhibit access into tight areas and impede fluid break off and make wicking of fluid up the exterior of the needle more pronounced. Some design variations have thinner walls produced from more elastic polymers. They suffer from deflection of the walls as a result of the pressure required at high flow rates, at shut off wall relaxation causes unwanted fluid bolus.

Ceramic needles are generally manufactured using the ceramic injection molding process. Using sophisticated mixing technology the powders are compounded with thermoplastic binders to produce feedstock pellets. The binders form a liquid medium that carries the ceramic powders into the mold during the injection stage. Molded parts then go through two thermal processes. First is pyrolysis or another method of de-binding to remove the binder, followed by sintering in a high temperature kiln to form the ceramic component. During sintering the component shrinks uniformly by as much as 20% but retains the complex shape. Parts are molded over size to account for this shrinkage. This process is costly, more suitable to low volumes and produces a needle that may be porous and prone to brittle fracture.

The approach to building a conjunct or unitized nozzle assembly utilizes several different processes each best suited for their intended purpose. A deep drawn nozzle core of monolithic construction is used to provide a contiguous fluid path. The fluid path has a thin wall and a smooth interior surface. It is free of imperfections that cause roughness. The thin wall enables the exit aperture to be a much larger diameter for a given gage size than the aforementioned needles used as the prior art items of commerce in industry today. A retention device capable of retaining the nozzle core under pressure is important to successful implementation and promulgation of the unitized or conjunct nozzle design style. Successful connection of the nozzle core to the hub is a key aspect. It is accomplished by molding the hub with the required material present that can be re-flowed and formed into a ledge overhanging the flange on top of the tapered core to provide a mechanical lock to prevent separation of the parts. Connection is enabled without the use of adhesives or ancillary devices. The unitized or conjunct style combines the advantageous features of low cost, thin wall, complete thread, color coding for size indication, contiguous path monolithic structure, minimal run-out, smooth interior surfaces and precise apertures to produce a precision part suitable for use on automated devices that require precision deposition of fluids.

Objects and Advantages

Accordingly, the design and the method of making unitized nozzle assemblies have inherent objects and advantages that were not described earlier in my patent. Several additional objects and advantages of the present invention are:

(1.) To provide a method of connecting a deep drawn nozzle core to a molded polymer retention device by re-flowing polymer material using heat and pressure to achieve a mechanical lock.

(2.) To provide a design for polymer retention device that contains the geometry necessary to minimize movement of material to enable re-flow to occur rapidly.

(3.) To provide a design for a polymer retention device that enables a volumetric match of the material re-flowed to the molded geometry apriori of re-flow.

(4.) To provide a design for a polymer retention device that enables assembly of core to hub without the use of adhesives to permanently bond the components together.

(5.) To provide a method of tooling the connection process of a deep drawn nozzle core to a molded polymer retention device that can prevent re-flow of the polymer into the interior standard taper where connection to a fluid source is facilitated.

(6.) To provide a method of tooling the connection process of a deep drawn nozzle core to a molded polymer retention device that can prevent heating of the thermally conductive metal core to enable the polymer retention device to maintain elasticity, not yield or elongate in order to retain compression against the core to prevent rotational movement of the core in the assembled state.

(7.) To provide a design for a polymer retention device that enables the deep drawn metal core to be inserted into the molded polymer retention device and stop at a constant depth to ensure re-flowed polymer volume cross section is consistent part to part to achieve constant strength and rigidity.

(8.) To provide a design for a polymer retention device that has a flat surface opposite of the opening the metal core is inserted into to support and resist the compressive load required to form the mechanical lock.

(9.) To provide a design for a polymer retention device that has geometry that can be located and centered easily in the tool used for support during processing.

(10.) To provide a design for a polymer retention device that maintains a concentric relationship of the polymer retention device to the deep drawn nozzle core to ensure it is rotatable in service.

(11.) To provide a method of tooling the connection process of a deep drawn nozzle core to a molded polymer retention device that uses a tool with elementary geometry that can be easily maintained and fabricated without the use of complex machine tools.

(12.) To provide a design for a polymer retention device that has an undercut inherent in the polymer hub that allows for automated movement of the polymer hub to the fixture where automated assembly to the deep drawn core occurs.

(13.) To provide a design for a polymer retention device that contains a square extrusion of sufficient size to gain leverage for use tightening and loosening the retention device.

(14.) To provide a design for a polymer retention device that can be molded in colors chosen to denote deep drawn core aperture size without requiring use of a mark on the deep drawn core for indication.

(15.) To provide a design for a polymer retention device that can provide space for a concave company designator for component recognition.

SUMMARY OF THE INVENTION

The invention is a novel method of design and manufacture for a polymer retention device specifically built to connect to a deep drawn nozzle core. Nozzle cores require an interface to prevent separation from the standard taper under pressure generated by transmission of fluid. A polymer nozzle assembly comprises:

A thin walled deep drawn nozzle core that has a cylindrically shaped tapered wall parallel to the angle formed by a standard taper inserted into a conically shaped hole that is congruent to the thin tapered wall of the nozzle core where it mates to the standard luer taper designed for connection to a source of pressurized fluid. A shaped circular fossa is conjoined to the top of the conically shaped cavity that extends through the polymer hub. A cusp of circular shape extends upward from the surface the shaped circular fossa originates. Width of the cross section and height of the cusp of circular shape is a function of the volume required to form an invaginated or enclosed cavity with a thickness substantial enough to support a load equivalent to the force required to separate the core from the standard taper. Volume of the formed or solidified profile that supports the required force for separation is equal to the volume of the circular shaped cusp. Separation force great enough to pull the seated nozzle core from the standard luer taper is generated by means of a contiguous thread around the circumference of the polymer hub. Below the contiguous thread is a square shaped cross sectional profile that provides a means to apply additional torque to the polymer retention device and forms a fundus circumscribed by the minimum diameter of the thread. The fundus profile is preferred to be flat and parallel to the top of the circularly shaped cusp that extends upward from where the fossa originates. However, the fundus shape can have a profile that is radial or conical. A core inserted into the tapered cylinder shaped hollow fits with interference and is pressed into the polymer hub until the exterior flare wall is coincident to the bottom of the circular shaped fossa. Interior edge of the fossa that is adjacent to the tapered cylinder shaped hollow is relieved by installation of an interior edge chamfer that prevents the exterior flare wall radius from interfering with the coincident relationship of exterior flare wall with the bottom of the circular shaped fossa. Pressing the core into the hollow until exterior flare wall bottoms, forces the walls of the polymer hub to expand outward creating a pressure acting inward that grips the cylindrically shaped tapered wall of the core inhibiting rotation in service.

Application of a compressive load combined with heat is required to soften the polymer enough so it can be guided to form an invaginated or inwardly turned enclosed cavity to encapsulate the flange of the nozzle core. This is accomplished through use of a press combined with resistive heating elements as known in the prior art. A shaped metallic rod with a profile designed to manipulate the heated polymer into the solidified profile is required. The topside of the core flange is adjacent to the ledge formed by the inwardly turned enclosed cavity after solidification and functions to capture the flange of the nozzle core. Ejection of the nozzle core in service is facilitated by formation of the ledge at the top of the invaginated cavity providing a tensile or thrust force through rotation acting on a radial inclined plane that forms the thread.

To manufacture the connection between the polymer hub and the nozzle core, support of the fundus is required, this is accomplished by placing the polymer hub or core retention device into a cylindrical cavity or counter-bore that circumscribes the square cross sectional profile or form a concave geometry with sides that are adjacent to the cross sectional profile shape that forms the lower portion of the polymer retention hub in a support block with a hole. Geometric shapes such as triangles, hexagons, pentagons, circles or the like can also be used to form the cross sectional profile that forms the lower portion of the polymer retention device as long as the shapes are properly sized to maintain a fit that is concentric with the counter-bore contained in the support block or form a shaped cavity or nest with sides that are adjacent to the cross sectional profile shape formed by the hub with generous relief at corners to ease insertion and removal. A core is inserted into the tapered hollow in the polymer hub. A hole in the center of the counter-bore, shaped cavity or nest extends through the support block to provide the clearance required for the protruding portion of the taper terminus to reside. This prevents unintended impacts and unintended damage that could result during formation of the enclosed turned in cavity around the core flange.

The ledge-form tool is a heated hollow cylinder of highly thermally conductive metal that contains a spring-loaded button made of non-thermally conductive material. It articulates inward to supply a downward force against the interior radius of the nozzle core flange to provide a shut off that prevents excess melted polymer from ingress into the tapered cylindrical wall. Shut-off button action not only prevents sealing failure from contaminates that could migrate during manufacture between the tapers when components are connected eventually in service but it also provides an interior wall to direct the softened polymer to form the interior shape of the edge to the solidified profile. Sacrifice of the salient circular cusp during this procedure is made to provide the softened polymer material required for re-flow to produce a ledge that overhangs the nozzle core flange. The top of the core flange is adjacent to the underside of the overhung ledge that serves to lock the top of the nozzle core flange into the polymer retention device. Solidification produces a ledge with a top surface that is parallel to the fundus. However, other sectional profiles like radii adjacent to the core flange perimeter, faceted flats or some combination can be used for support of load that is not necessarily parallel to the fundus.

These and other objects of the invention will become clearer when one reads the following specification taken together with the drawings that are attached hereto. The scope of protection sought by the inventor may be gleaned from a fair reading of the Claims that conclude this specification.

DESCRIPTION OF THE DRAWINGS—FIGURES

Turning now to the drawings wherein elements are identified by numbers and like elements are identified by like numbers throughout the seven figures, a drawing of the nozzle core with a partial cut away at the top and close up cut away "A" of the bottom of the nozzle is depicted in FIG. 1.

DESCRIPTION OF THE PREFERRED EMBODIMENT

Figure 1:
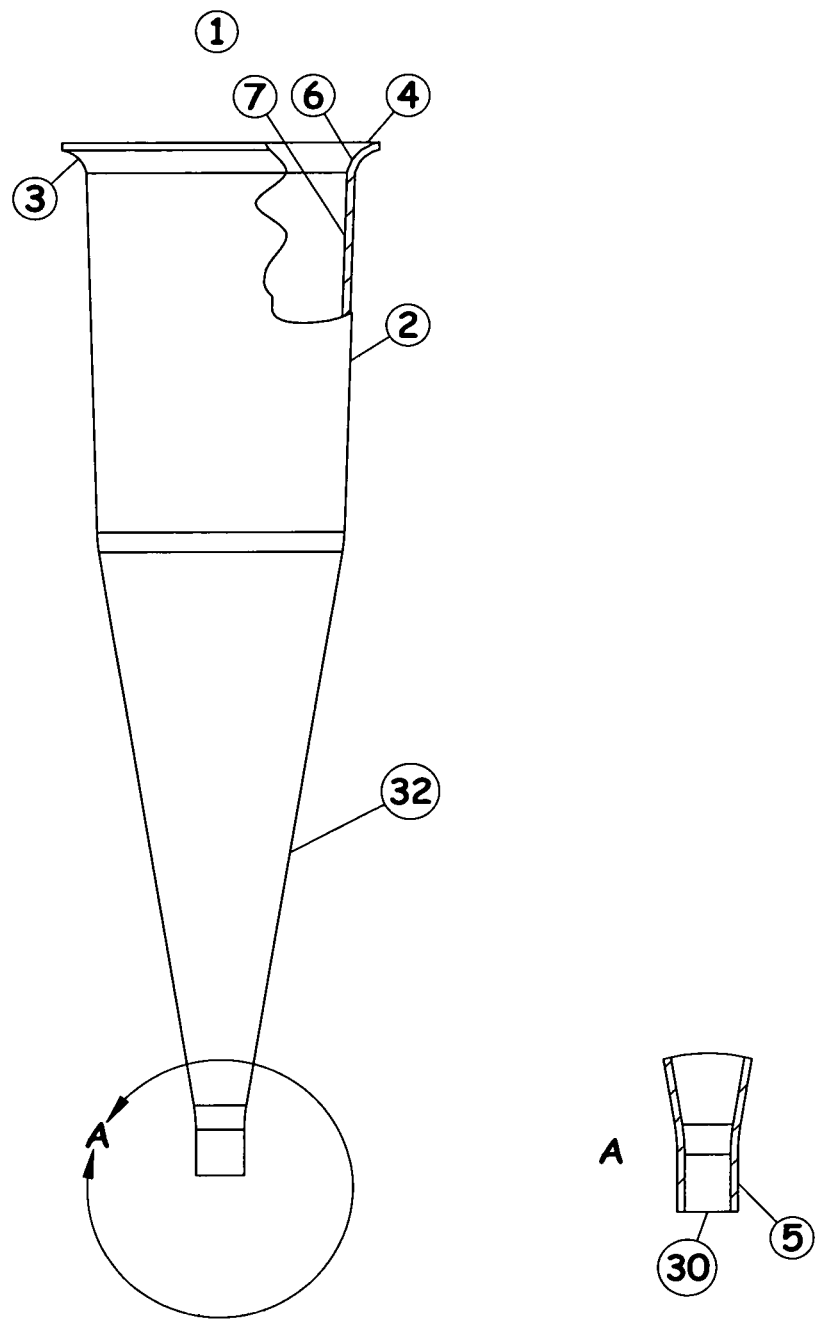
Figure 8:
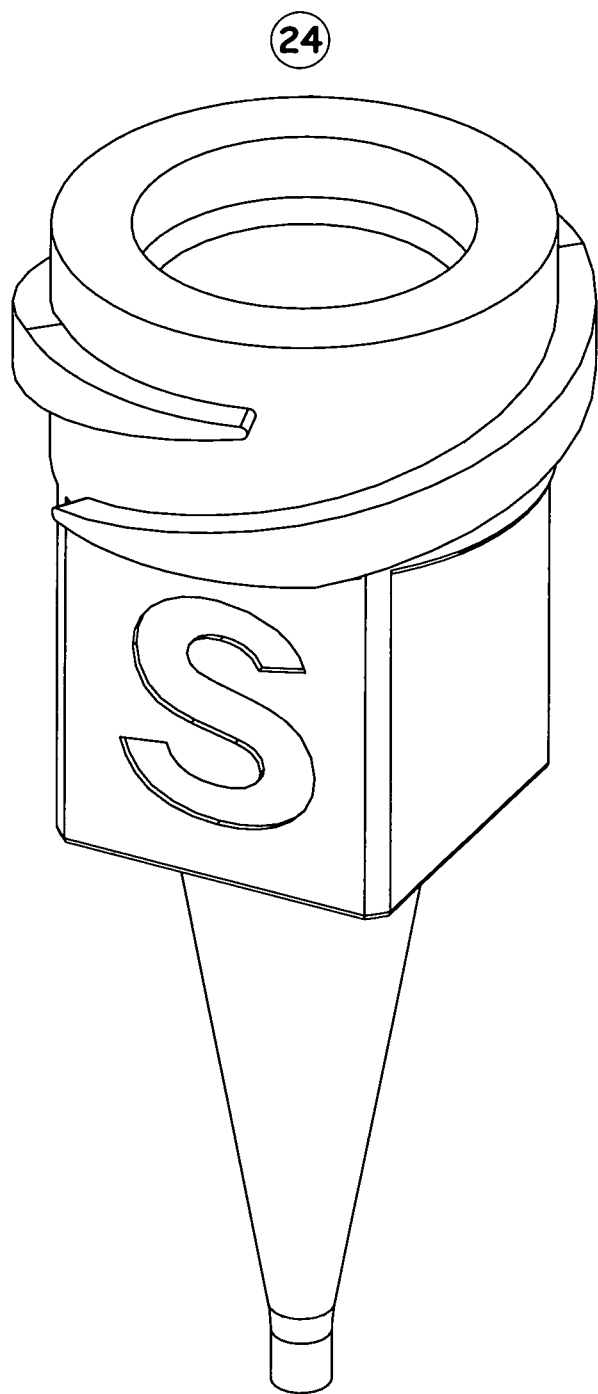
FIG. 8 is an illustrative view of the finished polymer retention device permanently fastened to the nozzle core to form a unitized or conjunct nozzle looking downward from an elevated vantage point downward.

Referring now to the drawings wherein the showings are for the purpose of illustrating preferred embodiments of the invention only and not for the purpose of limiting it. The invention is a novel manner of creating and a technique of assembling a conjunct nozzle 24 of which the outcome is depicted in FIG. 8. FIG. 1 shows the thin wall nozzle core 1 in a vertical, attitude, as it would be inserted and captured in a retention device 8 and used in service in the industry. The deep drawing process is used to produce the core 1 that is depicted in the illustration. A thin walled deep drawn nozzle core 1 has a tapered exterior cylindrical wall 2 parallel to the angle formed by a standard luer taper as is known in the prior art. Exterior cylindrically shaped barrel wall 2 or exterior shaped barrel wall 2 extends downward to an exterior conically shaped wall 32 that is attached to a taper terminus 5. Terminus 5 is extruded downward to the extent the structure necessary to form an exit aperture 30 is provided. Cores 1 are designed with an exterior flare wall 3 that forms the basis for a flange 4. The interior nozzle core flange radius 6 provides a nozzle core 1 interior surface that enables a shut-off button 20 to locate, seat and activate to supply downward force necessary for prevention of re-flowed polymer from entering and blocking the interior cylindrically shaped barrel wall 7. This ensures an interior thin tapered wall 7 that mates with a standard luer taper as is known in the prior art is free of contaminates that would cause unwanted extrication of fluid through the standard luer taper from transmission pressure due to an interruption of mating sealing surfaces. Contact of the shut-off button 20 against the interior upper flared opening radius 6 also allows formation of the shaped edge 23 of the cantilevered solidified profile formed by re-flow of the salient cusp 9.

Figure 2:
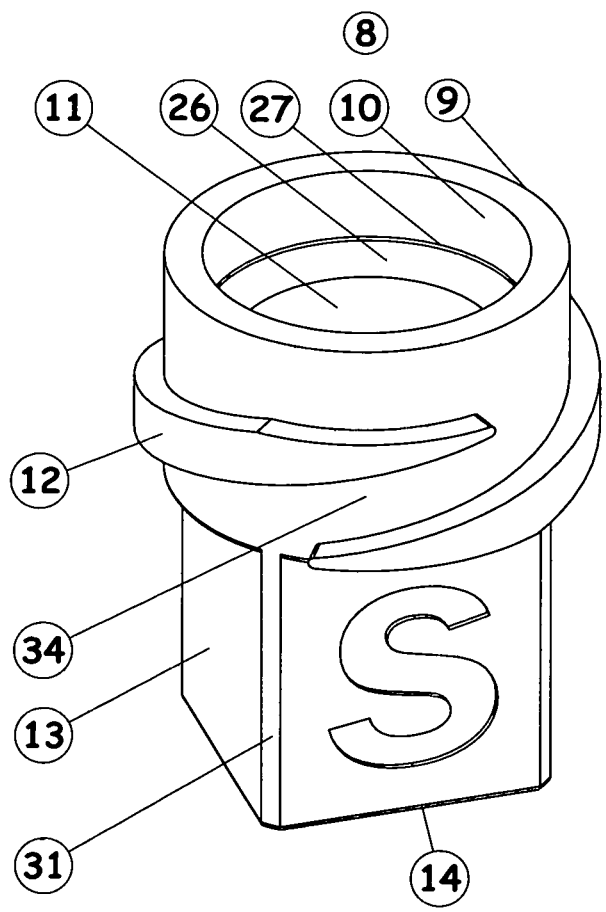
FIG. 2 is an illustrative view of the polymer retention device from a vantage point looking downward at an angle and a view looking directly at the fundus of the retention device.
Figure 2:
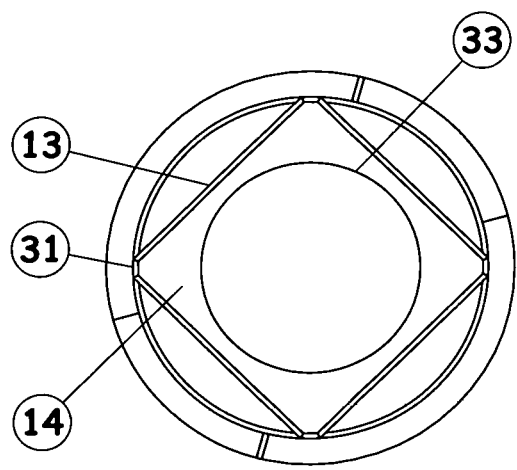

FIG. 2 is a view of the polymer retention device 8 in a vertical orientation as produced by the plastic injection molding process as is known in the prior art before insertion of a thin wall nozzle core 1. A shaped circular fossa 10 is conjoined to the top of the conically shaped cavity 11 that extends down to a cylindrical relief 33 that cuts through the remainder of the polymer hub 8 breaking out through the fundus 14 center. Interior edge relief 26 of the fossa 10 that is adjacent to the tapered cylinder shaped hollow 11 is relieved by installation of a interior edge chamfer 26 that prevents exterior flare wall radius 3 from interfering with the coincident relationship of exterior flare wall 3 with circular shaped fossa bottom 27. A circular shaped cusp 9 extends upward from the surface the shaped circular fossa 10 originates. Width of the cross section and height of the circular shaped cusp 9 is a function of the volume required to form an invaginated cavity 18 with a thickness substantial enough to support a load equivalent to the force required to separate the core 1 from the standard luer taper that connects it to the source of fluid. Volume of the formed or solidified profile that supports the required force for separation is equal to the volume as molded of the circular shaped cusp 9. Separation force great enough to pull the seated nozzle core 1 from the standard luer taper is generated by means of a radial inclined plane 12 around the circumference of the polymer hub 8.

Below the contiguous thread 12 is a square shape cross section 13 that could be designed as a round, triangular, pentagonal, hexagonal, octagonal or other shaped cross sectional geometry. A square shaped cross section 13 is selected to provide a means to apply additional torque to the polymer retention device 8 to maximize flat length for the small size of the retention device 8 that surrounds the nozzle core 1 to facilitate application of torque away from the weaker corner radii 31 to the center of the flat of the square cross section 13 where strength is greater for a polymer hub 8.

A fundus 14 is formed with corner radii 31 that are the result of the fundus 14 circumscribed by the minimum root diameter 34 of the thread 12. The fundus 14 has a profile that is flat and parallel to the top of the circularly shaped cusp 9 that extends upward from where the fossa 10 originates. However, the fundus 14 can assume radial or conical profiles that are other than flat or parallel to the salient cusp 9.

The sequence of steps required assembling and forming the connection between the polymer retention device 8 and the nozzle core 1 is a key aspect to the novel method of manufacturing a unitized nozzle assembly 24. To accurately show the order of operations required, FIGS. 3, 4, 5 are displayed as cut away views of each step that is required to make the connection with the process.

Figure 3:
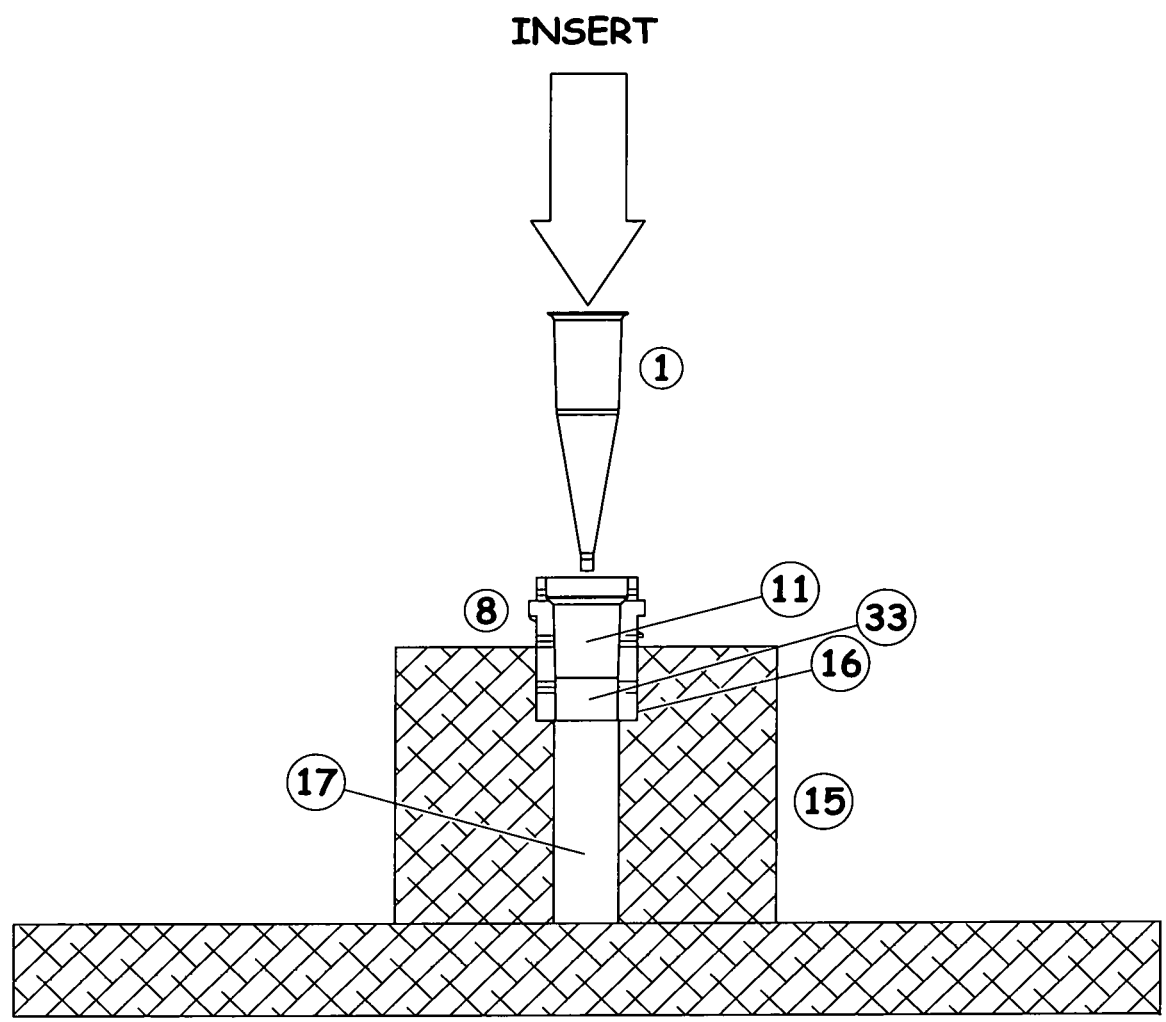
FIG. 3 is an illustrative view of a nozzle core being manipulated into a cut away view of the polymer retention device seated in a support block.

FIG. 3 is a partial cut away illustration of the first step in the manufacture of the conjunct nozzle 24. To make a connection between the polymer hub 8 and the nozzle core 1, support of the flat fundus 14 is required, this is accomplished by placing the polymer hub 8 or core retention device 8 into a cylindrical cavity 16 or counter-bore 16 that circumscribes the square cross section 13 that forms the lower portion of the polymer retention hub 8 in a support block 15 with a through hole 17. A core 1 is inserted in the direction indicated by the arrow into the tapered hollow 11 in the polymer hub 8.

Figure 4:
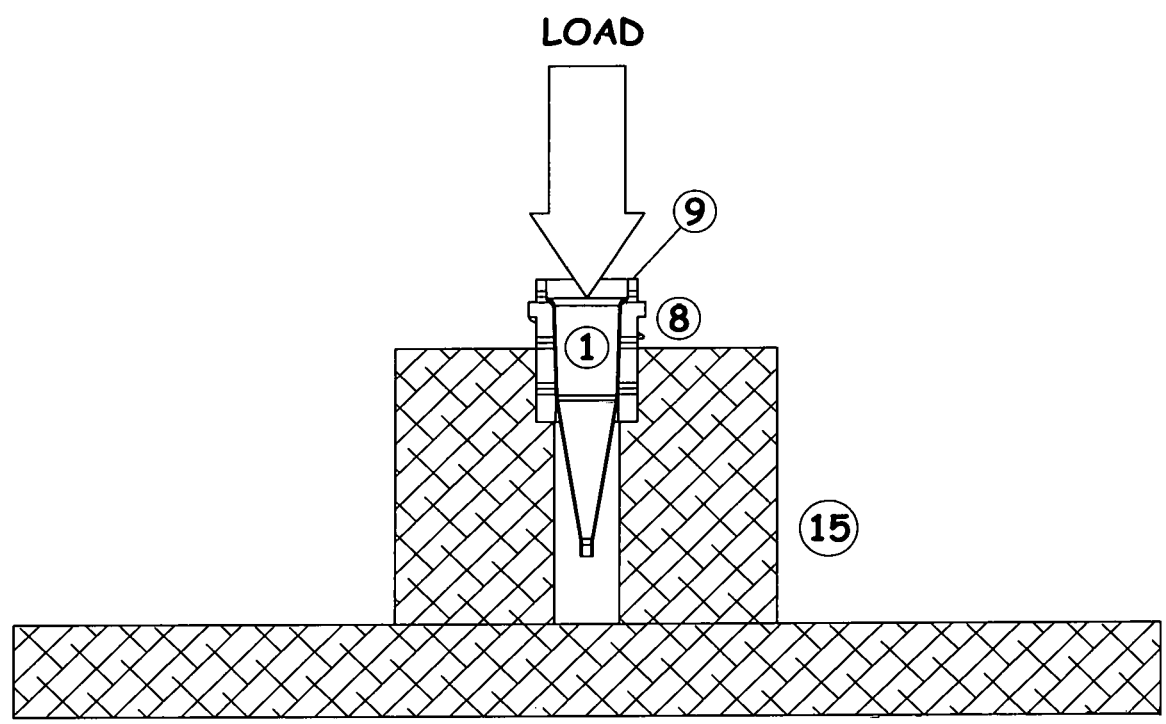
FIG. 4 is a sectional cut away view of the nozzle core as a load is directed and it is pressed into the polymer retention device seated in the support block.

FIG. 4 shows application of a load to the core 1 that is sufficient to seat the exterior flare wall 3 into the shaped circular fossa 10. Load is applied until the exterior flare wall 3 is seated against the circular shaped fossa bottom 27 such that interior edge chamfer 26 does not impede the coincident relationship. This forces the tapered hollow 11 of the polymer hub 8 to expand outward creating pressure acting inward. The pressure exerted is a function of the elastic behavior of the polymer. Appropriate tolerances enable expansion within the elastic limit of the material to provide a force that grips the cylindrically shaped tapered wall 2 of the core 1 and helps to inhibit rotation in service when the unitized polymer hub nozzle assembly 24 is installed and removed from standard luer tapers. A hole 17 in the center of the counter-bore 16 that extends through the support block 15 provides clearance required for the protruding portion of the taper terminus 5 to reside. This protects cores 1 by preventing unintended impact and damage that can result during formation of the enclosed cavity 18 around the core flange 4.

Figure 5:
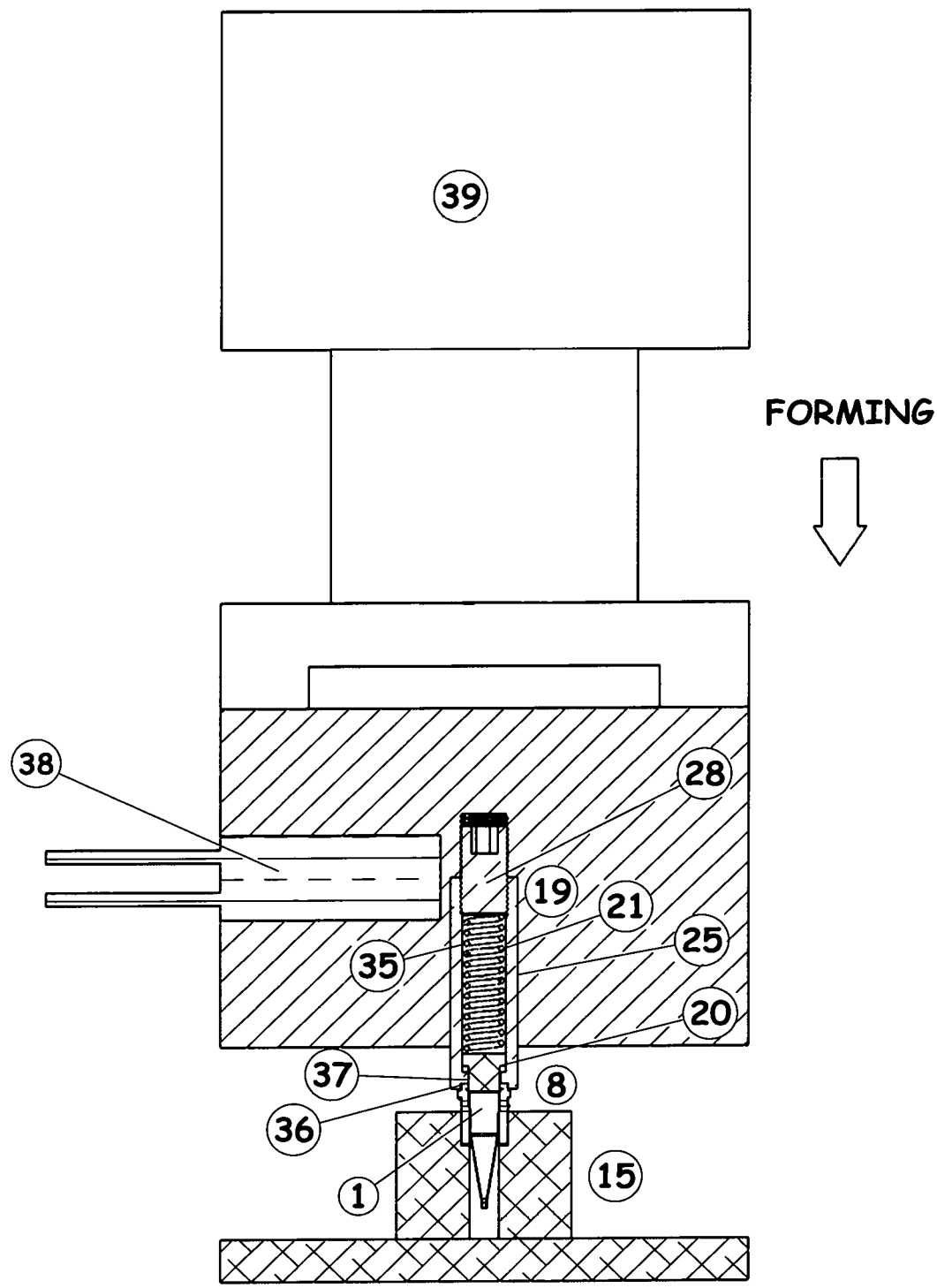
FIG. 5 is a partial sectional cut away view of the polymer retention device seated in a support block at the end of the assembly cycle with shut off button depressed and ledge profile formed over the nozzle core flange.

FIG. 5 depicts the last step in the process of formation of the connection of the polymer retention device 8 to the thin walled deep drawn nozzle core 1. Support of the polymer hub 8 is achieved by insertion into the cylindrical cavity 16 contained in the support block 15. The through hole 17 prevents unintended impact and damage to the terminus 5 of the thin wall nozzle core 1 that results during formation of the invaginated cavity 18 around the core flange 4. Counter bore 16 with a hole 17 in a support block 15 is aligned in a concentric manner to the ledge form tool 19 thereby enabling the retention device 8 to locate suitably within the counter-bore 16 and allow the thin walled core 1 to maintain concentricity. This ensures the ledge-form tool 19 will operate correctly and the button 20 will make contact in the required location on the tapered interior cylindrical wall 7 of the thin walled deep drawn nozzle core 1. Force and thermal energy is applied to the forming tool 19 through the cylindrical housing 25 by a thermal press or some other such device as is known in the prior art.

The ledge-form tool assembly 19 is heated and made from highly thermally conductive metal that forms a heated hollow cylinder 25 and contains a spring-loaded button 20 made of non-thermally conductive material. Cylindrical housing 25 contains a deep counter-bore 35 that provides a cavity to contain a force compliant member 21 and a shallow circular depression 36 on the opposite side. A small diameter hole 37 provides the necessary geometry for fit of a button 20. Button 20 articulation is inward against a force compliant member 21 that pushes against a threaded cap 28 and supplies a downward load against the interior radius of the nozzle core flange 6 to provide a shut off that prevents excess melted polymer from ingress into the tapered interior cylindrical wall 7. Shut-off button 20 action not only prevents sealing failure from contaminate occupation between mating taper surfaces when components are connected eventually in service but it also provides an interior wall to direct the softened polymer to form the interior shape of the edge or shaped edge 23 to the solidified profile. The button 20 also provides force to aid separation upon completion of formation of the overhang 22. Sacrifice of the salient circular cusp 9 during this procedure is made to provide the softened polymer material volume required for re-flow to produce a ledge 22 that forms an overhang 22 to produce the enclosed cavity 18 to trap the nozzle core flange 4. The top of the core flange 4 is adjacent to the underside of the overhung ledge 22 that serves to lock the top of the nozzle core flange 4 into the polymer retention device 8. Solidification produces a ledge 22 with a top surface that is parallel to the fundus 14.

Figure 6:
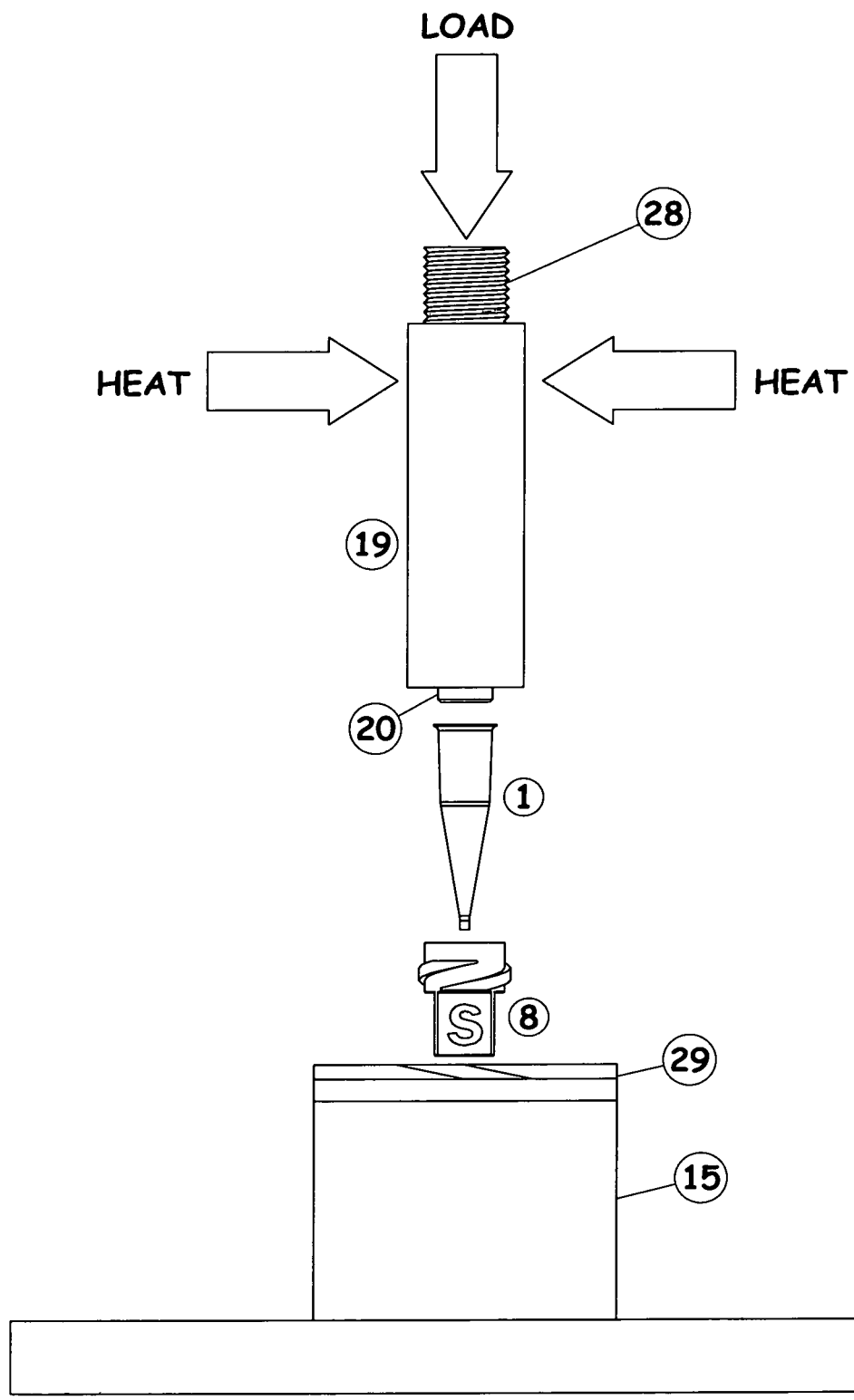
FIG. 6 is a front view of the assembly system components necessary to perform the process of connection of polymer retention hub to nozzle core.

FIG. 6 is a front view illustration of tools, component parts of the design, force and energy required to initiate forming the unitized nozzle 24. Each of the elements used in the process are arranged in a serial fashion to denote the sequential nature of the operation. The load required to generate pressure substantial enough to re-flow the polymer softened by exposure to the elevated temperature of the ledge form tool 19 is shown schematically using a vertically oriented arrow labeled load and two horizontal arrows labeled heat. Energy is applied to the top of the thermally conductive hollow cylindrical housing 25 the form tool 19 is constructed from. The threaded cap 28 contains the force compliant member 21 to provide a solid structure for the force compliant member 21 used to energize the button 20 to push against interior radius of nozzle core flange 6. A clamp 29 aids separation of a newly formed conjunct nozzle 24 from the spring-loaded button 20 of the ledge-form tool 19. Implementing a restraint 29 ensures a newly formed conjunct nozzle assembly 24 is not lifted from the block 15 in an uncontrolled fashion and damaged inadvertently at the end of the operation. Restraint can be accomplished by translation of a clamp 29 mounted at the top of the support block 15 for lock up of radial inclined plane 12 preventing pull out of conjunct nozzle 24 from nest 16 or by exertion of force against a face of the square shaped cross section 13 or a corner radius 31 of polymer hub 8 shaped as a round, triangular, square, pentagonal, hexagonal, octagonal or other shaped geometry to form an alternate cross section for a nozzle 24 against a datum surface or side wall in a counter bore 16 that is round 40, triangular, square 41, pentagonal, hexagonal, octagonal or other shaped geometry. A square shaped 41 counter bore 16 with sides that are adjacent to the square shaped cross section 13 formed by the polymer hub 8 has generous relief 41 at corners to ease insertion and removal. Retraction of the shaped metallic rod 19 leaves a conjunct nozzle 24 trapped by a restraint 29 in the block 15, withdrawal of the clamp 29 and removal of a finished conjunct nozzle assembly 24 completes the operation.

Figure 7:
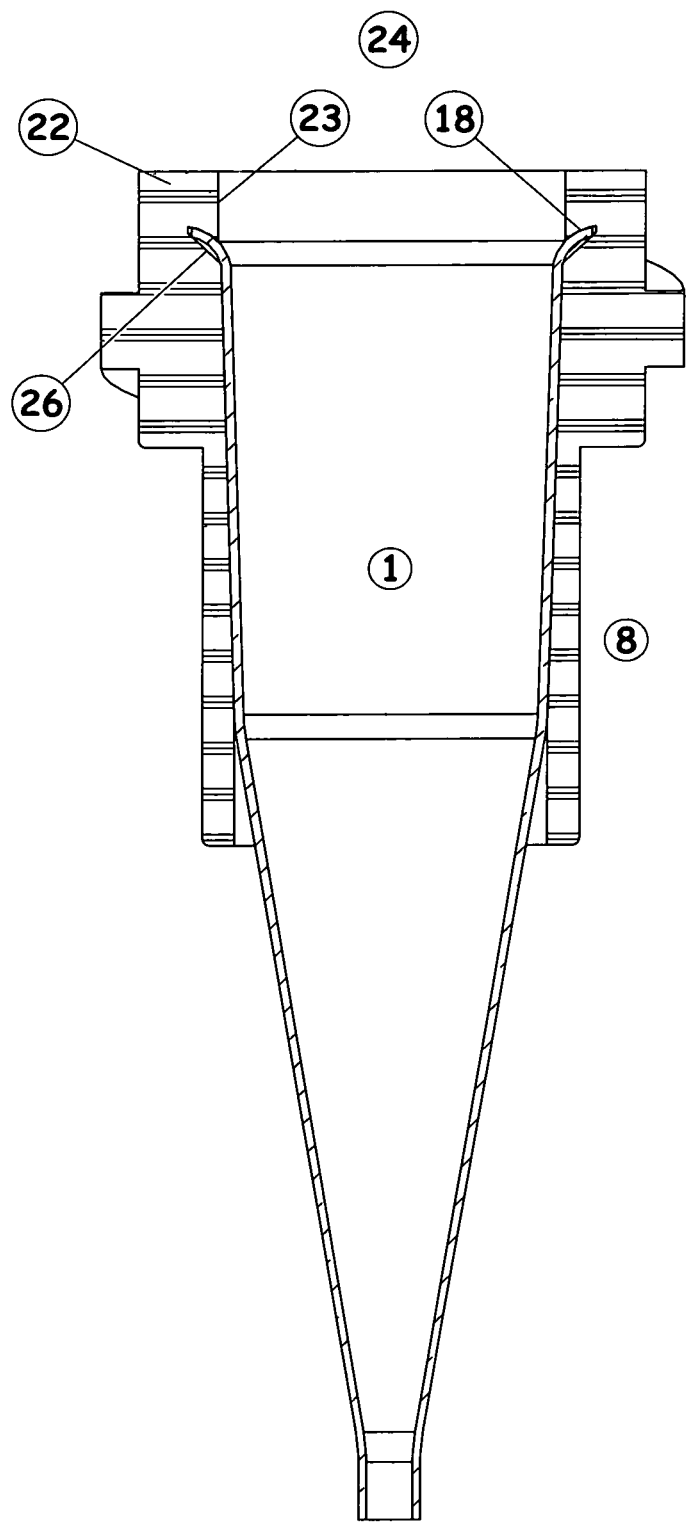
FIG. 7 is a cut away section view of a conjunct nozzle showing illustrative details of connection.

FIG. 7 is a full section view of a complete conjunct nozzle 24. Core 1 is captured in the polymer retention hub 8 by the overhung ledge 22 that forms an invaginated cavity 18. A shaped edge 23 is produced upon retraction of the shut off button 20 from the upper flared opening 6 as shaped metallic rod 19 withdrawals after completion of the forming operation.

FIG. 8 is a pictorial representation of a finished unitized nozzle assembly 24 from a slightly elevated vantage point looking downward. A unitized polymer nozzle 24 has a polymer hub 8 permanently attached to the nozzle core 1. The nozzle 24 is pointing downward as it would most likely be used in service in the industry. Conjunct nozzle 24 sizes are denoted by a discrete polymer retention hub 8 color for each thin walled nozzle core 1 corresponding with a unique exit aperture size 30. Manufacture of the nozzle assembly 24 using this method is easily automated and is accomplished without the use of adhesive that slows the process and elevates risk of contamination though migration of excess adhesive by misapplication.

Figure 9:
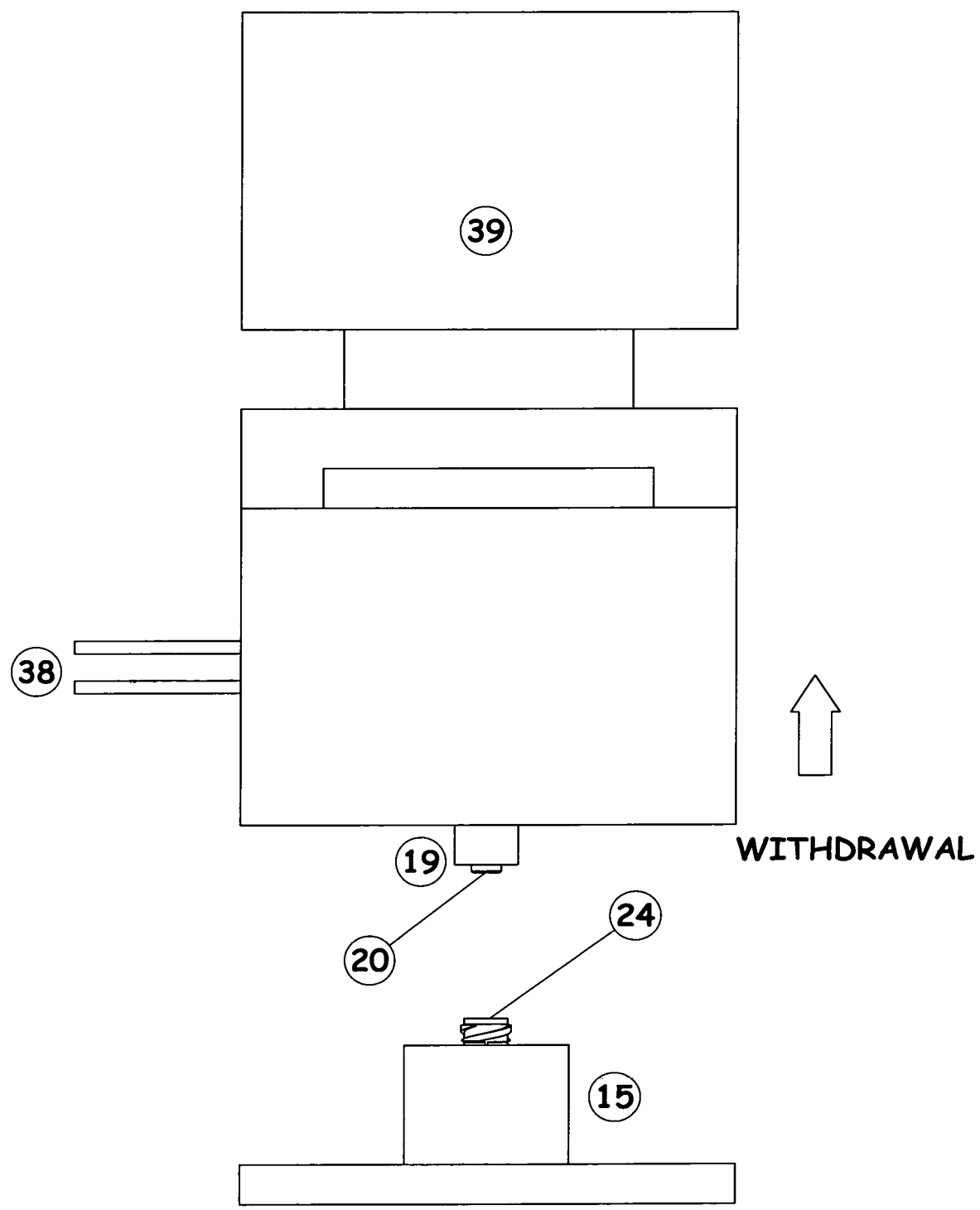
FIG. 9 shows a view of front side of a forming tool apparatus, a support block, a unitized nozzle assembly and a press with a heating element that provides a means to withdrawal a ledge-form tool assembly after forming a conjunct nozzle.

FIG. 9 is an illustration from a level vantage point looking directly ahead showing a front view of a thermal press 39 with a ledge-form tool assembly 19 installed. Press 39 with a resistive heating element 38 retracts, withdrawaling a ledge-form tool 19 after forming. A spring-loaded button advances 20 and a conjunct nozzle 24 remains in the support block 15.

Figure 10:
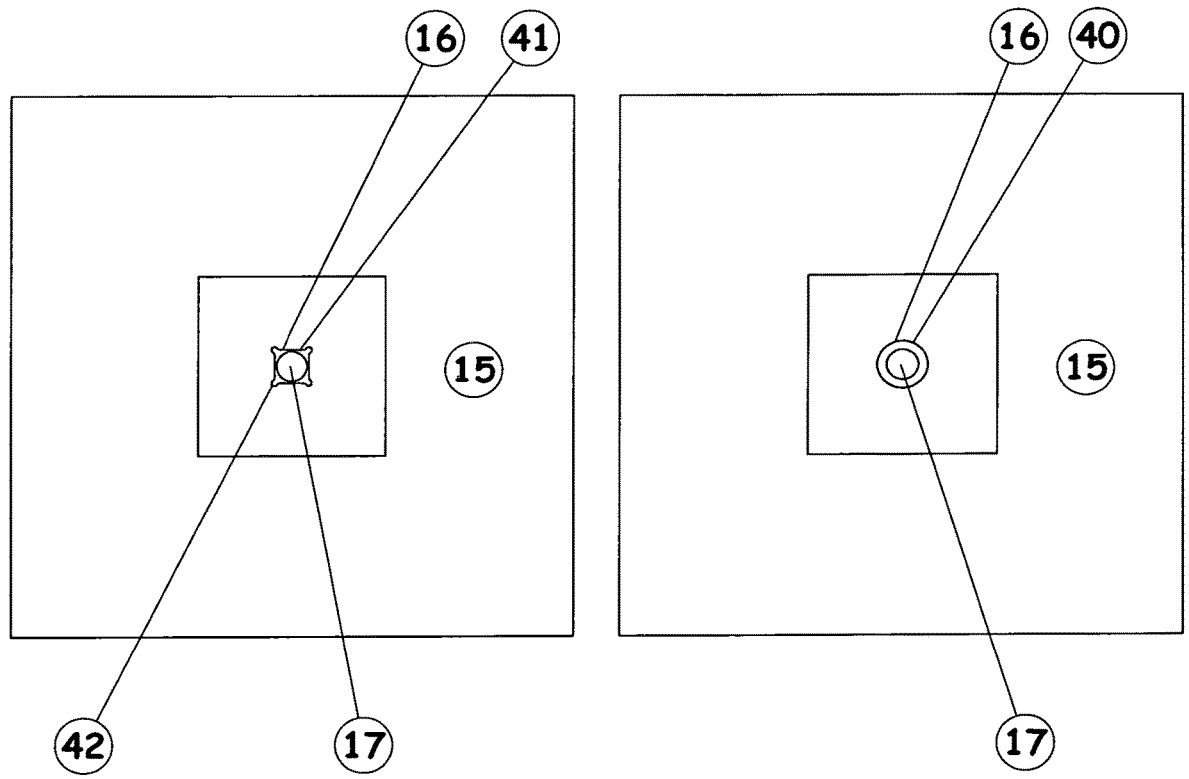
FIG. 10 is a view of two support blocks looking from an overhead vantage point looking directly downward, a square nest with a generous relief at corners and a round nest with a hole in the center are shown.

FIG. 10 is an overhead view looking downward at two support blocks 15 each support block 15 shows a nest 16 or counter-bore 16 with a hole 17 in the center, a square nest 41 with generous relief 42 at the corners and a round nest 40 are shown.

While the invention has been described with reference to a particular embodiment thereof, those skilled in the art will be able to make various modifications to the described embodiment of the Invention without departing from the true spirit and scope thereof. It is intended that all combinations of elements and steps, which perform substantially, the same function in substantially the same way to achieve substantially the same result, be within the scope of this invention.

What is claimed is:

1. A forming tool apparatus for a press having a heating element, comprising:
    a) a cylindrical housing with a deep counter-bore on one end having a shallow circular depression opposite end of said deep counter-bore and a small diameter hole through a wall in-between each end that separates said deep counter-bore end from said shallow circular depression end;
    b) a button with a large diameter side and a small diameter side slideably fit inside said deep counter-bore end and into said small diameter hole;
    c) a force compliant member fit inside said deep counter-bore end presses against said button on said large diameter side;
    d) a threaded cap fit into said deep counter-bore end pushes against said force compliant member; and
    e) a support block below that contains a nest having a through hole located in center of said nest, said nest further includes, a concave shaped cavity having sides that are adjacent to a cross sectional profile shape established by a square shape cross section and wherein shaped geometry other than said square shape cross section used to establish said lower portion entails configuration of said concave adjacent sides of said nest to said cross sectional profile shape of said shaped geometry other than said square shape cross section.

2. The forming tool apparatus for the press having the heating element of claim 1, wherein said cylindrical housing is made of metal.

3. The forming tool apparatus for the press having the heating element of claim 1, wherein said button is made of non-thermally conductive material.

4. The forming tool apparatus for the press having the heating element of claim 1, wherein components of said cylindrical housing and said support block having said nest are coaxially aligned.

5. The forming tool apparatus for the press having the heating element of claim 1, wherein said small diameter side of said button limits size of softened polymer surrounding said button to diameter of said small diameter side.

6. The forming tool apparatus for the press having the heating element of claim 1, further including a restraint by having translation of a clamp mounted on top of said support block wherein pull out from said nest is prevented.

7. The forming tool apparatus for the press having the heating element of claim 1, further including said nest in said support block configured to have sides that form a square counter bore with a flat bottom surface or a circular counter bore with said flat bottom surface wherein said through hole in center of said nest is concentrically aligned with said button.

8. The forming tool apparatus for the press having the heating element of claim 1, wherein said heating element contiguous with said cylindrical housing on said press elevates temperature of said cylindrical housing and said press applies force downward until contact is made pushing said button upward, deflecting said force compliant member permitting said cylindrical housing with said shallow circular depression to contact a surface and thereby soften and form polymer contained within said shallow circular depression.

9. The forming tool apparatus for the press having the heating element of claim 1, wherein having heated a polymer from contact with said shallow circular depression end of said cylindrical housing; contiguously attached to said heating element, urging of said press directs softened polymer material around said small diameter of said button.

10. The forming tool apparatus for the press having the heating element of claim 1, wherein retraction of said cylindrical housing extends said button thereby assisting separation of said shallow circular depression from contact with softened polymer after completion of forming operation.

11. The forming tool apparatus for the press having the heating element of claim 1, further including a conjunct nozzle, wherein withdrawal distance of said cylindrical housing after use exposes said nest thereby permitting removal of said conjunct nozzle.

12. A ledge form tool apparatus fora press having a heating element, comprising:
   a) a thermally conductive hollow cylindrical housing contiguously attachable to said heating element to provide a heated hollow cylinder on said press, said heated hollow cylinder has a shallow circular depression on one end;
   b) a shut-off button having a large diameter and a small diameter that has a close clearance slidable fit in a small diameter hole located through said shallow circular depression;
   c) a deep counter-bore end having a force compliant member sandwiched between a threaded cap and said large diameter of said shut-off button; and
   d) a support block having a nest suitably sized, positioned in said press, said nest further includes, a concave shaped cavity having sides that are adjacent to a cross sectional profile shape established by a square shape cross section and wherein shaped geometry other than said square shape cross section used to establish said lower portion entails configuration of said concave adjacent sides of said nest to said cross sectional profile shape of said shaped geometry other than said square shape cross section.

13. The ledge form tool apparatus for the press having the heating element of claim 12, wherein said support block with said nest mounted under said heated hollow cylinder is concentric to said shallow circular depression to surround an exterior thereby transfer heat rapidly to soften and form a polymer.

14. The ledge form tool apparatus for the press having the heating element of claim 12, wherein said force compliant member pushes against said shut-off button having said shut-off button extend and apply a load to insert by said press.

15. The ledge form tool apparatus for the press having the heating element of claim 12, wherein said force compliant member yields having said shut-off button retract and said shallow circular depression apply load and transfer heat for forming by said press.

16. The ledge form tool apparatus for the press having the heating element of claim 12, wherein withdrawal of said heated hollow cylinder following forming is arranged, permitting said force compliant member inside to recover from yield and extend said shut-off button in contact with a surface, pushing said surface away from said shallow circular depression thereby aiding separation from a softened polymer.

17. The ledge form tool apparatus for the press having the heating element of claim 12, wherein said shut-off button is made of a material that is non-thermally conductive to prevent conductive heat transfer from contact with said shut-off button.

18. The ledge form tool apparatus for the press having the heating element of claim 12, wherein said small diameter hole is centered in said shallow circular depression.

19. The ledge form tool apparatus for the press having the heating element of claim 12, wherein said small diameter of said shut-off button is limited to a diameter sized to obstruct a standard luer taper from entry of a polymer softened through heat.

20. A ledge form tool apparatus comprising:
   a) a block with a counter bore with a nest that further includes, a concave shaped cavity having sides that are adjacent to a cross sectional profile shape established by a square shape cross section and wherein shaped geometry other than said square shape cross section used to establish said lower portion entails configuration of said concave adjacent sides of said nest to said cross sectional profile shape of said shaped geometry other than said square shape cross section;
   b) a thermally conductive hollow cylindrical housing made of metal centered over said counter bore that contains a force compliant member situated between a threaded cap and a button made of non-thermally conductive material;
   c) a shallow circular depression surrounding a small diameter hole for fit of said button on end of said thermally conductive cylindrical housing opposite; said threaded cap; and
   d) a source of controlled heat.

* * * * *